US011731991B2

(12) United States Patent
Laskin et al.

(10) Patent No.: US 11,731,991 B2
(45) Date of Patent: Aug. 22, 2023

(54) AUGMENTING MOIETIES FOR ANTI-INFLAMMATORY COMPOUNDS

(71) Applicants: Rutgers, The State University of New Jersey, New Brunswick, NJ (US); Lehigh University, Bethlehem, PA (US)

(72) Inventors: Jeffrey D. Laskin, Piscataway, NJ (US); Diane E. Heck, Rumson, NJ (US); Carl J. Lacey, New Tripoli, PA (US); Ned D. Heindel, Easton, PA (US); Sherri C. Young, Bloomsbury, NJ (US)

(73) Assignees: LEHIGH UNIVERSITY, Bethlehem, PA (US); RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 66 days.

(21) Appl. No.: 16/991,440

(22) Filed: Aug. 12, 2020

(65) Prior Publication Data
US 2020/0369688 A1 Nov. 26, 2020

Related U.S. Application Data

(60) Continuation-in-part of application No. 16/022,019, filed on Jun. 28, 2018, now Pat. No. 10,752,582, which is a continuation of application No. 15/365,088, filed on Nov. 30, 2016, now Pat. No. 10,570,161, which is a division of application No. 13/127,284, filed as application No. PCT/US2009/005971 on Nov. 3, 2009, now abandoned, said application No. 16/022,019 is a continuation of application No. 15/334,882, filed on Oct. 26, 2016, now abandoned, which is a continuation-in-part of application No. 14/776,857, filed as application No. PCT/US2014/028329 on Mar. 14, 2014, now Pat. No. 9,512,068.

(60) Provisional application No. 61/793,842, filed on Mar. 15, 2013, provisional application No. 61/790,870, filed on Mar. 15, 2013, provisional application No. 61/198,147, filed on Nov. 3, 2008.

(51) Int. Cl.
| | |
|---|---|
| C07F 7/08 | (2006.01) |
| A61K 31/405 | (2006.01) |
| A61K 31/196 | (2006.01) |
| A61K 31/19 | (2006.01) |
| A61K 47/55 | (2017.01) |
| A61K 9/00 | (2006.01) |
| A61K 31/192 | (2006.01) |
| C07C 69/96 | (2006.01) |
| C07C 229/42 | (2006.01) |
| C07D 209/28 | (2006.01) |
| A61K 47/54 | (2017.01) |

(52) U.S. Cl.
CPC .......... *C07F 7/0812* (2013.01); *A61K 9/0014* (2013.01); *A61K 31/19* (2013.01); *A61K 31/192* (2013.01); *A61K 31/196* (2013.01); *A61K 31/405* (2013.01); *A61K 47/54* (2017.08); *A61K 47/55* (2017.08); *C07C 69/96* (2013.01); *C07C 229/42* (2013.01); *C07D 209/28* (2013.01); *C07F 7/081* (2013.01); *C07C 2602/10* (2017.05)

(58) Field of Classification Search
CPC .... A61K 31/19; A61K 31/192; A61K 31/196; A61K 31/405; A61K 47/54; A61K 47/55; A61K 9/0014; C07C 229/42; C07C 233/56; C07C 2601/14; C07C 2601/16; C07C 2602/10; C07C 271/16; C07C 271/34; C07C 271/48; C07C 69/96; C07D 209/28; C07F 7/081; C07F 7/0812
See application file for complete search history.

(56) References Cited

U.S. PATENT DOCUMENTS

| | | | |
|---|---|---|---|
| 3,983,178 A | 9/1976 | Pattison et al. | |
| 4,206,310 A | 6/1980 | Mukaiyama et al. | |
| 4,420,490 A | 12/1983 | Sallmann et al. | |
| 4,443,473 A * | 4/1984 | Buckwaiter | A61K 8/44 514/487 |
| 4,639,438 A | 1/1987 | Sehring et al. | |
| 4,681,897 A * | 7/1987 | Brand | A61P 25/04 514/557 |
| 5,082,964 A | 1/1992 | Heindel et al. | |

(Continued)

FOREIGN PATENT DOCUMENTS

| | | |
|---|---|---|
| DE | 3223949 A1 | 12/1983 |
| EP | 0289262 A2 | 11/1988 |

(Continued)

OTHER PUBLICATIONS

National Center for Biotechnology Information (Feb. 20, 2008). PubChem Compound Summary for CID 24078980 from https://pubchem.ncbi.nlm.nih.gov/compound/24078980 (Year: 2008).*

(Continued)

*Primary Examiner* — Kara R McMillian
(74) *Attorney, Agent, or Firm* — Fox Rothschild LLP

(57) ABSTRACT

Augmented or synergized anti-inflammatory constructs are disclosed including anti-inflammatory terpenes and/or vanilloids covalently conjugated to one another so that the activity of the conjugate is greater than the sum of its parts. Also disclosed are methods of improving the potency of an anti-inflammatory terpene or vanilloid by linking it to another anti-inflammatory terpene or vanilloid via a carbamate linkage, where the potency of the conjugate is greater than the sum of its parts.

9 Claims, No Drawings

(56) References Cited

U.S. PATENT DOCUMENTS

| | | | |
|---|---|---|---|
| 5,434,170 | A | 7/1995 | Andrulis, Jr. |
| 8,889,736 | B2 * | 11/2014 | Maniar .................. A61P 29/02 514/544 |
| 9,512,068 | B2 | 12/2016 | Laskin et al. |
| 2005/0234244 | A1 | 10/2005 | Bartolini et al. |
| 2008/0107720 | A1 | 5/2008 | Walters et al. |
| 2009/0238905 | A1 | 9/2009 | Gurney et al. |
| 2011/0133121 | A1 | 6/2011 | Shinohata et al. |

FOREIGN PATENT DOCUMENTS

| | | | |
|---|---|---|---|
| WO | 2004017967 | A1 | 3/2004 |
| WO | 2006036994 | A2 | 4/2006 |
| WO | 2006/054832 | A1 | 5/2006 |
| WO | WO-2010089421 | A2 * | 8/2010 ............... A61K 8/42 |

OTHER PUBLICATIONS

Amitai et al. "Bifunctional Compounds Eliciting Anti-inflammatory and Anti-cholinesterase Activity as Potential Treatment of Nerve and Blister Chemical Agents Poisoning" Journal of Applied Toxicology 2006 26:81-87.
Appendino et al. "Chemoselective Esterification of Phenolic Acids and Alcohols" Organic Letters 2002 (22):3839-3841.
Bosse et al. "Synthesis and SAR of novel 1,1-dialkyl-2(1H)-naphthalenones as potent HCV polymerase inhibitors," Bioorganic & Medicinal Chemistry Letters (2008); 18:568-570.
Boyle et al. "Synthesis and Study of Thiocarbonate Derivatives of Choline as Potential Inhibitors of Acetylcholinesterase" Journal of Medicinal Chemistry 1997 40:3009-3013.
Brenner et al. "Arylcholine Carbonates and Aryl-3,3-dimethly-l-butyl Carbonates as Inhibitors and Inactivators of Acetylcholinesterase" Inhibitors and Inactivators of Acetylcholinesterase. Synthesis and Chemistry of Agrochemicals IL Washington, D.C.: ACS Publishers, 1991. 469-477.
Buck et al. "Chlorthiophos(S 2957)and Its Related Compounds; Chemistry and Biological Activity" VIII International Congress of Plant Protection, Papers at Sessions 1975 3(1):119-127.
But et al. "The Mitsunobu Reaction: Origin, Mechanism, Improvements, and Applications" Chemistry—An Asian Journal 2007 2:1340-1355.
Carey et al. "Part A: Structure and Mechanisms," Advanced Organic Chemistry, Fifth Edition (2007); p. 299.
Chang et al. "Therapeutic Potential of a non-steroidal bifunctional anti-inflammatory and anti-cholinergic agent against skin injury induced by sulfur mustard," Toxicoloy and Appliced Pharmacology (2014); 280:236-244.
Cohen et al. "Effects of Charge, Volume, and Surface on Binding of Inhibitor and Substrate Moieties to Acetylcholinesterase" Journal of Medicinal Chemistry 1985 28(9):1309-1313.
Dahan et al. "A Novel Mechanism for Oral Controlled Release of Drugs by Continuous Degradation of a Phospholipid Prodrug Along the Intestine: In-vivo and In-vitro Evaluation of an Indomethacin-Lecithin Conjugate" Journal of Controlled Release 2007 119:86-93.
Detoisien et al. "The Condensation of Lignin Model Compounds with Hexamethylene Diisocyanate", British Polymer Journal, 1985, vol. 17, No. 3, pp. 260-262.
Dvir et al. "DP-155, a Lecithin Derivative of Indomethacin, is a Novel Nonsteroidal Antiinflammatory Drug for Analgesia and Alzheimer's Disease Therapy" CNS Drug Reviews 2007 13(2):260-277.
Farias et al. 2005, Neurobiology of disease, vol. 18, pp. 176-183.
Fontana et al. "Cytochrome P450 Enzymes Mechanism Based Inhibitors: Common Sub-structures and Reactivity" Current Drug Metabolism 2005 6:413-454.
Gacem et al. "Esterification of sterically hindered acids and alcohols in fluorous media," Tetrahedron Letters (2003); 44:1391-1393.
Halen et al. "Combining Anticholinergic and Anti-Inflammatory Activities into a Single Moiety: A Novel Approach to Reduce Gastrointestinal Toxicity of Ibuprofen and Ketoprofen" Chemical Biology and Drug Design 2007 70:450-455.
Halen et al. "Substituted Aminoalcohol Ester Analogs of Indomethacin With Reduced Toxic Effects" Medicinal Chemistry Research 2007 16:101-111.
Inestrosa, et al. " The Role of Wnt Signaling in Neuronal Dysfunction in Alzheimer's Disease" Molecular Neurodegeneration 2008 3(9): 1-13.
Jain, et al. "QSAR Analysis of Indomethacin Derivatives as Selective COX-2 Inhibitors", Internet Electronic Journal of Molecular Design, Apr. 2006, vol. 5, No. 4, pp. 224-236.
Kalgutkar et al. "Ester and Amide Derivatives of the Nonsteroidal Antiinflammatory Drug, Indomethacin, as Selective Cyclooxygenase-2 Inhibitors" Journal of Medicinal Chemistry 2000 43:2860-2870.
Kwiecien et al. "Nitric Oxide (NO)-Releasing Aspirin and (NO) Donors in Protection of Gastric Mucosa Against Stress" Journal of Physiology and Pharmacology 2008 59(Suppl 2):103-115.
Dno et al. "A Convenient Procedure for Esterification of Carboxylic Acids" Bulletin of the Chemical Society of Japan 1978 51(8):2401-2404.
Østergaard et al. "Bioreversible Derivatives of Phenol. 2. Reactivity of Carbonate Esters with Fatty Acid-like Structures Towards Hydrolysis in Aqueous Solutions" Molecules 2007 12:2396-2412.
Prusakiewicz et al. "Comparison of Skin Esterase Activities from Different Species" Pharmaceutical Research 2006 vol. 23(7):1517-1524.
Rautio et al. "Prodrugs: Design and Clinical Applications" Nature Reviews Drug Discovery 2008 7:255-270.
Schumann et al. "Diallylaluminium-N,N- Dimethylaminoethanolate, the First Stable Allyl-Alane Suitable for Additions to Aldehydes, Ketones and Imines" Tetrahedron Letters 2002 43:3507-3511.
Streitwieser Jr., Andrew, "Solvolytic Displacement Reactions at Saturated Carbon Atoms," Chem. Rev. (1956); 56(4):585.
Sylvain et al. "An Efficient Procedure for the Esterification of Nitroacetic Acid: Application to the Preparation of Merrifield Resin-Bound Nitroacetate" Tetrahedron Letters 1999 40:875-878.
Tamaddon et al. "A Green Protocol for Chemoselective 0-Acylation in the Presence of Zinc Oxide as a Heterogeneous, Reusable and Eco-friendly Catalyst" Tetrahedron Letters 2005 46:7841-7844.
Vaddi et al. "Human Skin Permeation of Branched-Chain 3-0-Alkyl Ester and Carbonate Prodrugs of Naltrexone" Pharmaceutical Research 2005 22(5):758-765.
Venuti et al. "Synthesis and Biological Evaluation of Q-(N,N,N-Trialkylammonium)alkyl Esters and Thioesters of Carboxylic Acid Nonsteroidal Antiinflammatory Agents" Pharmaceutical Research 1989 6(10):867-873.
Wang et al. "Nicotinic Acetylcholine Receptor alpha-7 Subunit is an Essential Regulator of Inflammation" Nature 2003 421:384-388.
Wang et al. "Synthesis and Bioactivity of Novel Phthalimide Derivatives" Chinese Chemical Letters 2008 19:26-28.
Williams et al. "NO-Donating Aspirin Inhibits the Activation of NF-KB in Human Cancer Cell Lines and Min Mice" Carcinogenesis 2008 29(2):390-397.
Young, et al. "Peripheral Site Acetylocholinesterase Inhibitors Targeting Both Inflammation and Cholinergic Dysfunction", Biorganic & Medicinal Chemistry Letters, 2010, vol. 20, pp. 2987-2990.
Zimmer et al. Sterically Hindered Group IVA Organometallics VIH*. Preparation and Some Properties of Neohexyltin Compounds, J. Organometal, Chem. (1968); 14:222-224.
Zimmer et al. "Sterically Hindered Group IVA Organometallics. Preparation and Properties of Certain neopentyltins," J. Org. Chem (1964); 29(9):2632-2636.
Parduiz et al. "NSAIDs in the Acute Treatment of Migraine: A Review of Clinical and Experimental Data", Pharmaceuticals, 2010, 3, 1966-1987, doi: 10.3390/ph3061966.

* cited by examiner

AUGMENTING MOIETIES FOR ANTI-INFLAMMATORY COMPOUNDS

CROSS-REFERENCE TO RELATED APPLICATIONS

This application is a Continuation-In-Part of U.S. patent application Ser. No. 16/022,019, filed on Jun. 28, 2018, which is a Continuation of U.S. patent application Ser. No. 15/334,882, filed Oct. 26, 2016, which is a Continuation-In-Part of Ser. No. 14/776,857, filed on Sep. 15, 2015, now U.S. Pat. No. 9,512,068, which is the U.S. National Phase of International Patent Application Serial No. PCT/US14/28329, filed on Mar. 14, 2014, which claims the benefit of priority under 35 U.S.C. 119(e) of U.S. Provisional Application No. 61/790,870, filed on Mar. 15, 2013, and of U.S. Provisional Application No. 61/793,842, filed on Mar. 15, 2013. U.S. patent application Ser. No. 16/022,019 is also a Continuation-in-Part of Ser. No. 15/365,088, filed Nov. 30, 2016, now U.S. Pat. No. 10,570,161, which is a Divisional of U.S. patent application Ser. No. 13/127,284, filed Sep. 23, 2011, which is the U.S. National Phase of International Patent Application No. PCT/US09/05971, filed Nov. 3, 2009, which claims the benefit of priority under 35 U.S.C. 119(e) of U.S. Provisional Application No. 61/198,147, filed Nov. 3, 2008. The disclosures of all of the above are incorporated herein by reference in their entireties.

STATEMENT REGARDING FEDERALLY SPONSORED RESEARCH OR DEVELOPMENT

This invention was made with government support under Grant No. U54AR055073 awarded by the National Institutes of Health. The government has certain rights in the invention.

FIELD OF THE INVENTION

The invention is directed to anti-inflammatory compounds which are synergistically enhanced in their anti-inflammatory activity through conjugation with other specific anti-inflammatory components. Presently disclosed are methods of increasing the activity of an anti-inflammatory compound, which involve conjugating conjugating one, two or more anti-inflammatory compounds with each other, for example, terpene and/or vanilloid.

BACKGROUND OF THE INVENTION

The term "anti-inflammatory" refers to the property of a compound that reduces inflammation. Anti-inflammatory drugs make up about half of analgesics, remedying pain by reducing inflammation.

Nonsteroidal anti-inflammatory drugs (NSAIDs) are a class of drugs that provide analgesic and antipyretic (fever-reducing) effects, and, in higher doses, anti-inflammatory effects. The term "nonsteroidal" distinguishes these drugs from steroids, which, among a broad range of other effects, have a similar eicosanoid-depressing, anti-inflammatory action. As analgesics, NSAIDs are unusual in that they are non-narcotic. The most prominent members of the NSAID group of drugs are aspirin, ibuprofen and naproxen.

The widespread use of NSAIDs has meant that the adverse effects of these drugs are well known and have become increasingly prevalent as the population ages. The two main adverse drug reactions (ADRs) associated with NSAID use are gastrointestinal (GI) and renal effects. These effects are dose-dependent and, in many cases, severe enough to pose the risk of ulcer perforation, upper gastrointestinal bleeding, and death, thereby limiting the use of NSAID therapy. An estimated 10-20% of NSAID patients experience dyspepsia, and NSAID-associated upper GI adverse events are estimated to result in 103,000 hospitalizations and 16,500 deaths per year in the United States and represent 43% of drug-related emergency visits. Thus, the clinical problems with NSAIDs and the need for replacement anti-inflammatories are well recognized.

For at least these reasons, it would be desirable to find substitutes for the current NSAIDs having increased anti-inflammatory potency and a higher safety margin.

BRIEF SUMMARY OF THE INVENTION

It has now been discovered that one solution to this problem is to improve the potency and safety of anti-inflammatory compounds through the covalent combination of component anti-inflammatory moieties.

Terpenes and vanilloid platforms (e.g., 4-hydroxy-3-methoxybenzyl amine, commonly called vanillylamine; 4-hydroxy-3-methoxybenzyl alcohol, commonly called vanillyl alcohol; zingerone; [6]-paradol; and eugenol), are known to display modest anti-inflammatory and antinociceptive activity in animal and cellular models. In addition, aliphatic and alicyclic carbamates are known to be inhibitors of fatty acid amide hydrolase (FAAH), an enzyme whose inhibition is linked to anti-inflammatory effects. Thus, the individual components of the anti-inflammatory constructs of a first aspect of the invention, and the bonds that link them all together, provide a therapeutic benefit that can be greater than the sum of the parts.

It has now been discovered that the double and triple combinations of these anti-inflammatory components covalently linked together with at least one carbamate bond yields an augmented anti-inflammatory molecule whose net activity exceeds that of its individual building blocks. Some of these assemblies exceed the anti-inflammatory effects of the traditional NSAIDs.

The specific structural assemblies claimed herein include:
Formula 1 terpene-vanilloid
In some embodiments, the carbamate-linked structures have the following general structures:
Formula 1A terpene-(carbamate)-vanilloid
Related Analogs Include:
Formula 1B terpene-(carbamate)-terpene
Formula 1C vanilloid-(carbamate)-vanilloid
Specific examples of the components usable in construction of Formulae 1A to 1C anti-inflammatory conjugates include the following.

For terpenes: The terpene of the synergistic anti-inflammatory drug conjugate is selected from the group consisting of thymol, carvacrol, menthol, geraniol, nerol, farnesol, myrtenol, cumyl alcohol, citronellol, borneol, linalool, alpha-terpineol, and perillyl alcohol. If the drug construct contains more than one terpene molecule, they may be different or the same.

For vanilloids: The vanilloid moiety of the synergistic anti-inflammatory drug conjugate is selected from the group consisting of 4-hydroxy-3-methoxybenzyl amine commonly called vanillylamine, 4-hydroxy-3-methoxybenzyl alcohol commonly called vanillyl alcohol, zingerone, [6]-paradol, and eugenol. If the drug construct contains more than one vanilloid molecule, they may be different or the same.

DETAILED DESCRIPTION OF THE INVENTION

Surprisingly, it has now been discovered that weak anti-inflammatory moieties can be covalently linked by carbamate bonds to yield conjugate constructs of enhanced potency for suppression of inflammation.

One aspect of the present invention is directed to an anti-inflammatory conjugate where the anti-inflammatory component comprises at least one compound selected from the group consisting of anti-inflammatory terpenes and/or anti-inflammatory vanilloids.

A related aspect of the invention is directed to a method of improving the potency of an anti-inflammatory compound by linking it to another anti-inflammatory compound via a carbamate linkage, where the potency of the conjugate is greater than the sum of its parts.

In one embodiment of the present invention the terpene and/or vanilloid is not employed as a single component but as an augmenting component, covalently linked by a carbamate moiety to another anti-inflammatory moiety or to two other anti-inflammatory moieties, wherein they together serve to enhance or synergize performance. The conjugates may be bifunctional (meaning just two moieties) or trifunctional (meaning three components), or higher. In addition the carbamate linking bond itself can also convey anti-inflammatory activity to the conjugate.

Carbamate compounds are known to achieve anti-inflammation effect in vivo by inhibition of fatty acid amide hydrolase. In an inhibitory screen against fatty acid amide hydrolase (FAAH), the inventive carbamates were found to possess IC50 values which ranged from 9 µM to 1 mM for inhibition of FAAH. Some molecules were too lipophilic to dissolve in the enzyme assay medium and hence could not be tested. While there was no direct linear correlation between the compound's efficacy as an FAAH inhibitor and its potency in suppressing inflammation, many of the best inflammation suppressants were also FAAH inhibitors. The FAAH IC50 values are noted with the compound examples.

Hydrolysis of the conjugates can release the terpene or vanilloid, and any other co-anti-inflammatories to affect the therapeutic benefit in vivo.

A second case of decomposition that is too rapid can be seen in NDH4590 and 4593. Even though these compounds have impressive anti-inflammatory effects in the Mouse Ear Vesicant Model (MEVM) assay, their half-lives in sera or in any polar aqueous medium are comparatively short (hours). We have discovered that this is because the nucleophilic internal secondary amine NH executes an intramolecular nucleophilic attack on the carbonyl of the carbamate thereby freeing the terpene or the vanilloid component. This is a controllable, or tunable, chemically-induced hydrolysis that does not require an enzyme.

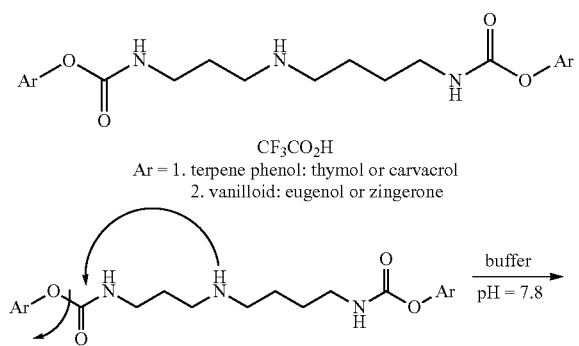

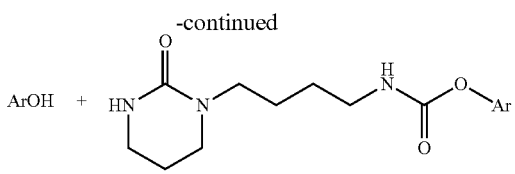

These compounds possess a terpene or vanilloid carbamate at both ends of the molecule in each case. With the unsymmetrical polyamine we have found that the cyclization occurs to form the six-membered ring only (versus a seven-membered ring).

Either making a salt (such as the trifluoroacetate, hydrochloride, mesylate, or other pharmaceutically acceptable salt) or a labile amide (for example, the trifluoroacetamide, trinitrobenzamide, or tris-trifluorobenzamide) on the internal NH solves the problem, and sufficiently long hydrolysis half-lives are then observed (days). The anti-inflammatory activity was unaffected by these stabilizing modifications, only the time of on-set of the effect was varied (cf. NDH4616, 4622, 4630, 4631, 4635, 4637 and 4649). Half-life for release can be controlled or tuned as noted above, by protonation or amide formation, but it can also be controlled by varying the nature of the anti-inflammatory leaving group. For example, zingerone is released much faster (half-life about 2 hours) than are carvacrol or thymol (half-lives about 2 days), which in turn are released much faster than an aliphatic terpene such as geraniol or borneol (marginal release after several days). The kinetics of release follow the typical organic moiety "leaving group" abilities.

PRESENT EMBODIMENTS

In one embodiment the anti-inflammatory compound is selected from the group consisting of anti-inflammatory vanilloids and ketone bodies. In another embodiment the vanilloid is selected from the group consisting of vanillyl alcohol, 3-methoxy-4-acetyloxybenzyl alcohol, and vanilylamine. In yet another embodiment the ketone body is selected from the group consisting of 3-hydroxybutyrate and homologues thereof. "Ketone bodies" such as 3-hydroxybutyrate and acetoacetate are produced as metabolites of fatty acids in the liver. 3-Hydroxybutyrate has inherent anti-inflammatory activity. For purposes of the present disclosure, a "homolog" or "homologue" is defined as a compound belonging to a series of compounds differing from each other by one or more methylene (—CH2—) groups, for example by a single methylene group. Thus 4-hydroxypentanoate and 3-hydroxypentanoate are both higher homologues of 3-hydroxybutyrate, depending on where in the carbon chain the methylene group has been inserted with respect to the hydroxy-bearing carbon of 3-hydroxybutyrate.

In addition to vanilloids and ketone bodies, other useful anti-inflammatory compounds include anti-inflammatory terpenes (e.g., geraniol, thymol, carvacrol, etc), anti-inflammatory hydroxy-cinnamic acids (e.g., ferulic acid, caffeic acid, and p-coumaric acid), anti-oxidants (e.g., cathecins/catechins and flavanols), indole-3-carbinol, pentoxifylline, and anti-inflammatory fatty acids (e.g., ricinoleic, palmitoleic, and docosahexaenoic).

In summary, one aspect of the invention is directed to an anti-inflammatory conjugate having the structure of Formula 1A terpene-(carbamate)-vanilloid, or Formula 1B terpene-(carbamate)-terpene, or Formula 1C vanilloid-(carbamate)-vanilloid; where the terpenes of Formula 1B and the vanilloids of Formula 1C are the same or different. The terpenes of the conjugate are independently selected from the group consisting of thymol, carvacrol, menthol, geraniol, nerol, farnesol, citronellol and perillyl alcohol. The vanilloids of the conjugate are independently selected from the group consisting of zingerone, eugenol, vanillyl alcohol, 3-methoxy-4-acetyloxybenzyl alcohol, paradol and vanillylamine. The conjugate can have the structure of Formula 1A. The conjugate can have the structure of Formula 1B. The terpenes of Formula 1B can be the same. The terpenes of Formula 1B can be different. The conjugate can have the structure of Formula 1C. The vanilloids of Formula 1C can be the same. The vanilloids of Formula 1C can be different. The anti-inflammatory activity of the conjugate is greater than the sum of its parts.

Another aspect of the invention is directed to a method of increasing the potency of an anti-inflammatory compound, comprising conjugating the anti-inflammatory compound with another anti-inflammatory compound via a carbamate linkage, to produce a conjugate where the structure of the conjugate is selected from the group consisting of Formula 1A terpene-(carbamate)-vanilloid, or Formula 1B terpene-(carbamate)-terpene, Formula 1C vanilloid-(carbamate)-vanilloid; where the terpenes of Formula 1B and the vanilloids of Formula 1C are the same or different. The anti-inflammatory activity of the conjugate is greater than the sum of its parts. The terpenes of the method are independently selected from the group consisting of thymol, carvacrol, menthol, geraniol, nerol, farnesol, citronellol and perillyl alcohol. The vanilloids of the method are independently selected from the group consisting of zingerone, eugenol, vanillyl alcohol, 3-methoxy-4-acetyloxybenzyl alcohol, paradol and vanillylamine. The conjugate of the method can have the structure of Formula 1A. The conjugate of the method can have the structure of Formula 1B. The terpenes of Formula 1B can be the same. The terpenes of Formula 1B can be different. The conjugate of the method can have the structure of Formula 1C. The vanilloids of Formula 1C can be the same. The vanilloids of Formula 1C can be different.

EXAMPLES

Materials and Methods

All reactants and solvents used were of the highest purity commercial grade and were employed without further purification. All reactions were performed in oven-dried apparatus under a nitrogen atmosphere, unless otherwise noted. All solvents used were anhydrous, unless otherwise noted. NMR spectra were recorded on a Bruker multinuclear spectrometer and chemical shifts are reported as ppm using tetramethylsilane (TMS) as an internal standard. 1H NMR spectra were recorded at 500 MHz, while 13C NMR spectra were recorded at 125 MHz. Elemental analyses were performed at Intertek (Whitehouse, N.J.). All thin layer chromatography (TLC) was performed on Analtech silica gel plates (250 microns).

Biological Evaluations
Ellman Assay

The modified Ellman assay for inhibition of acetylcholinesterase (AChE) and the mouse ear vesication assay (MEVA) have been described in detail by us (see S. C. Young et al, J Appl Tox, 2012, 32: 135-141). AChE (Type V-S from electrophorus electricus), acetylthiocholine iodide (ATChI), 5,5'-dithiobis(2-nitrobenzoic acid) (DTNB) and tacrine from EMD Chemicals (Gibbstown, N.J.). Cholinesterase inhibition was assayed spectrophotometrically at 412 nm according to Ellman's method. Assays were performed in polystyrene 96-well plates (Corning 96-well flat transparent) and a conventional micro-plate reader was employed for kinetic readings (Tecan Infinite 200 multimode). The following reagents were added to the wells: 200 µL of 0.5 mM DTNB in sodium phosphate buffer (100 mM, pH 8), 30 µL of inhibitor stock solution in methanol, 20 µL of 1.25 units/mL of AChE in sodium phosphate buffer (20 mM, pH 7), and 50 µL of 3 mM ATCh in buffer (100 mM, pH 8). Immediately after the substrate was added, the absorption signal was measured at 30 s intervals over 5 min at 25° C. Percentage inhibition was calculated relative to a negative control (methanol). The background signal was measured in control wells containing every reagent except for the substrate. IC50 values were obtained from a minimum of eight concentrations in duplicate and by fitting the experimental data with a dose-response curve using Prism software (Version 5.00, GraphPad Software, San Diego, Calif.).

Mouse Ear Vesicant Model (MEVM)

Animal studies were approved by the Rutgers University Institutional Animal Care and Use Committee and received human care in compliance with the institution's guidelines, as outlined in the Guide for the Care and Use of Laboratory Animals of the National Academy of Sciences. Compounds were assessed as inhibitors of inflammation using the MEVM as previously described (Casillas, R P., et al., Therapeutic approaches to dermatotoxicity by sulfur mustard. 1.Modulaton of sulfur mustard-induced cutaneous injury in the mouse ear vesicant model, J. Appl. Toxicol., 2000, 20, Suppl 1, S145-51), except that female CD-1 mice (4-6 weeks old) were used. Either CEES, chloroethyl ethyl sulfide (65 µmoles) or TPA, 12-O-tetradecanoylphorbol-13-acetate, (1.5 nmol) was used to induce inflammation. To evaluate each compound, ears (3-4 mice per group) were treated with 20 µL, of vehicle control (methylene chloride or acetone) or the test compound (1.5 µmol) in 20 µL, of the appropriate vehicle. After 5 h, mice were euthanized and ear punches (6 mm in diameter) were taken and weighed. Once the raw data were obtained, masses of ear punches were averaged and the percent reduction of vesicant-induced edema and inflammation was calculated using the method of Casillas et al. Raw data were analyzed using a one-way ANOVA to evaluate statistical significance ($P<0.05$).

Inflammation suppression, if observed, is of course dose related but is reported herein only at the standard dose mentioned above. Also, in some cases the anti-inflammatory candidate suppresses the mean weight of the ear punches from the test ears below that observed with the untreated control and these results are stated as >100% suppression.

Conjugates

The bifunctional and tri-functional conjugates of the invention were prepared and tested in a standard in vivo MEVM assay for their efficacy compared to that of the parent terpene or vanilloid from which each was assembled. Terpene inflammation suppression scores (average of TPA-induced and CEES-induced injuries) ranged from myrtenol (6%), thymol (14%), carvacrol (15%), cumyl alcohol (16%), geraniol (35%), menthol (38%), perillyl alcohol (43%), and farnesol (69%). All terpenes, except farnesol, had inflammation suppression scores less than 45%. The inflammation scores of typical vanilloids were similarly low and none exceeded 40%, e.g., vanillin (11%), vanillyl alcohol (31%), and vanillylamine (35%). In this assay inflammation suppression scores for the polyamines were under 30%.

The synergistic effects of combination of weakly potent anti-inflammatory components into conjugates are readily evident in the compounds of the invention. As an example of the Formula 1 class recited earlier herein, the terpene carvacrol by itself displayed inflammation suppression of 19% and 10% for CEES and TPA-induced inflammation respectively while its carbamate conjugate with vanillylamine (NDH4574) showed a significantly improved suppression of 89% and 88% (CEES and TPA).

Formula 1A class terpene-(carbamate)-vanilloid:

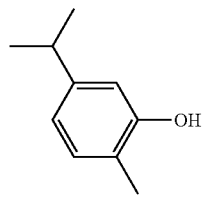

Carvacrol

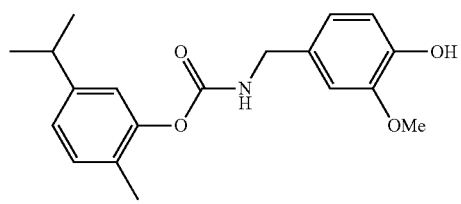

NDH4574

Another Formula 1 conjugate combines the terpene linalool to the vanilloid, vanillylamine, to yield the construct (NDH4624) which displayed a 92% suppression of CEES-induced inflammation.

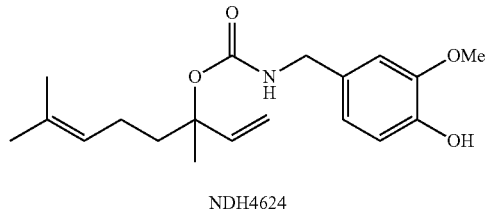 [SMILES: C=CC(C)(CCC=C(C)C)OC(=O)NCc1ccc(O)c(OC)c1]

NDH4624

As another example of the Formula 1 conjugate, the terpene (geraniol) coupled to the vanilloid (vanillylamine) by a carbamate linkage and designated as NDH4484 had a 64% suppression (CEES-induced injury) and a 71 µM inhibition of fatty acid amide hydrolase (FAAH).

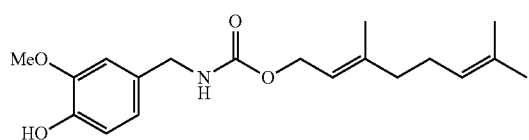

NDH4484

Similarly, a Formula 1 example involving perillyl alcohol showed the same trend with an inflammation suppression score of 43% (for the parent "free" terpene) while its carbamate conjugate with vanillylamine (NDH4498) showed an enhanced suppression of 53% (CEES) and 76% (TPA). This carbamate showed an IC50 for inhibition of fatty acid amide hydrolase (FAAH) of 14 µM.

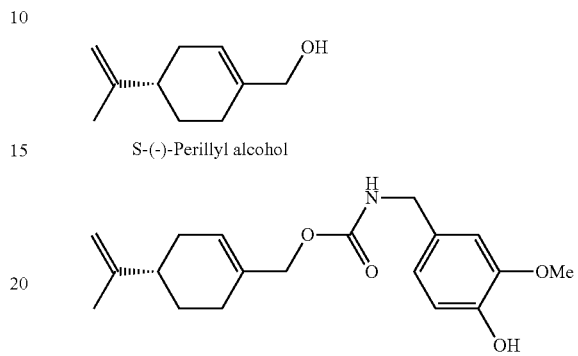

S-(-)-Perillyl alcohol

NDH4498

NDH 4501 (synthesized from farnesol and vanillylamine). Inflammation suppression of CEES-induced inflammation=79%:

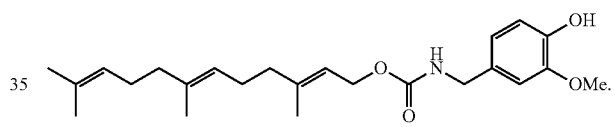

NDH 4506 (from geraniol and vanillylamine). Inflammation suppression of TPA-induced inflammation=105%:

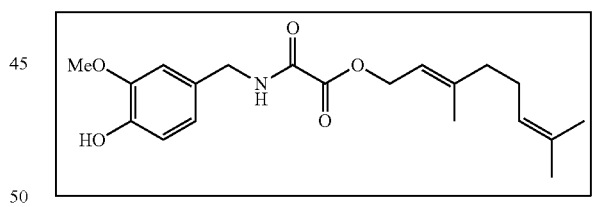

NDH 4541 (from menthol and vanillylamine). Inflammation suppression of CEES-induced inflammation=102%:

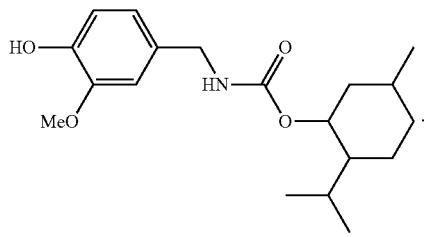 [SMILES: COc1cc(CNC(=O)OC2CC(C)CCC2C(C)C)ccc1O]

NDH 4546 (from citronellol and vanillylamine) Inflammation suppression of CEES-induced inflammation=66%. IC50 for FAAH inhibition 95 micromolar:

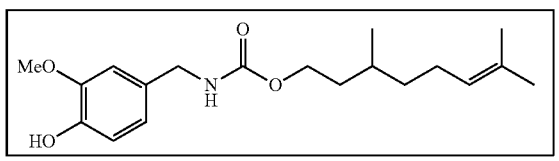 [SMILES: COc1cc(CNC(=O)OCCC(C)CCC=C(C)C)ccc1O]

Formula 1C class vanilloid-(carbamate)-vanilloid:
NDH 4626 (from the vanilloid eugenol and vanillylamine) Inflammation suppression of CEES-induced inflammation=67%:

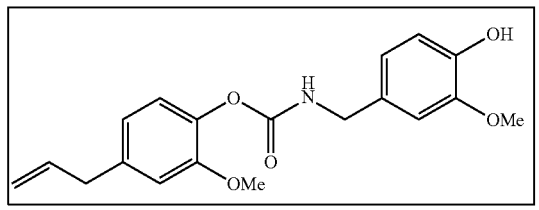

Similarly, the Formula 1B class shows positive inflammation suppression.

Synthesis

The compounds of the invention were synthesized by the pathways outlined in Schemes 1, 2, 3, 4, and 5, using the application of a thiazolide to transfer the —COOR unit to the polyamine, amine, or amino acid unit. The activated thiazoline is synthesized as shown in Scheme 2 if the terpene being transferred has a secondary hydroxyl group, otherwise the pathway as shown in Scheme 1 is suitable. Scheme 3 shows the transfer pathway for —COOR moiety to the polyamines. Scheme 3 shows how the internal secondary NH in the polyamine can have its nucleophilicity suppressed by salt formation or acetamide formation in order to prevent auto-decomposition. Scheme 4 shows how terpene and/or vanilloid moieties are transferred to an amino acid platform compound. Scheme 5 shows how terpene moieties are directly linked to vanilloid moieties (vanillylamine as example) to generate conjugates of Formula 1.

Scheme 1. Synthesis of N-alkyloxycarbonyl thiazolidine-2 thiones from 1° alcohols and N-aryloxycarbonyl thiazolidine-2 thiones from phenols: (R = terpene and/or vanilloid moiety). Suitable for alcohol moiety such as geraniol; suitable for phenol moieties such as carvacrol, thymol, eugenol, zingerone and paradol.

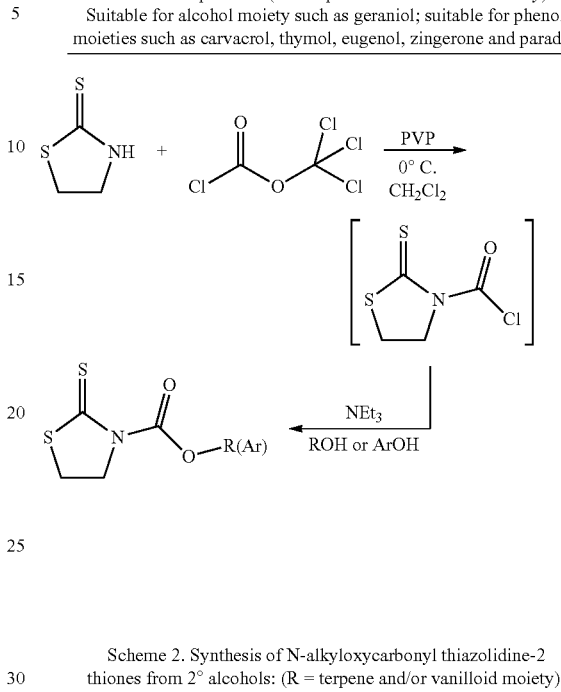

Scheme 2. Synthesis of N-alkyloxycarbonyl thiazolidine-2 thiones from 2° alcohols: (R = terpene and/or vanilloid moiety). Suitable for alcohol moiety such as borneol.

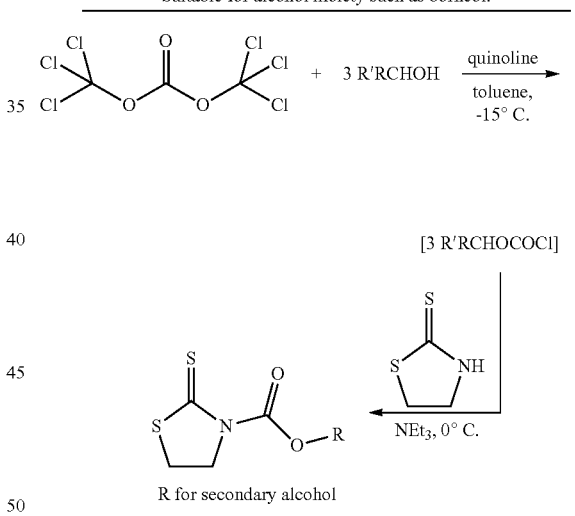

R for secondary alcohol

Scheme 3. Synthesis of salts and acetamides of polyamine conjugates: (R = terpene and/or vanilloid moiety)

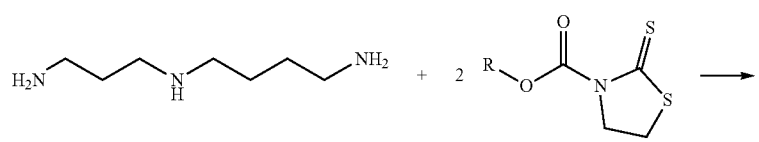

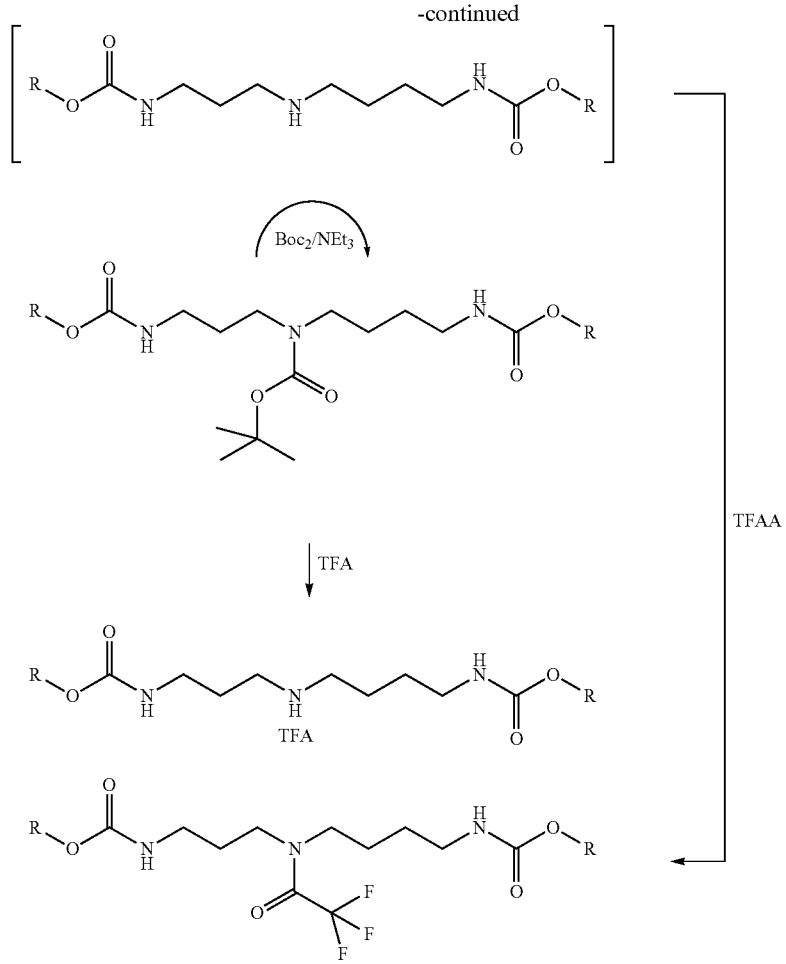
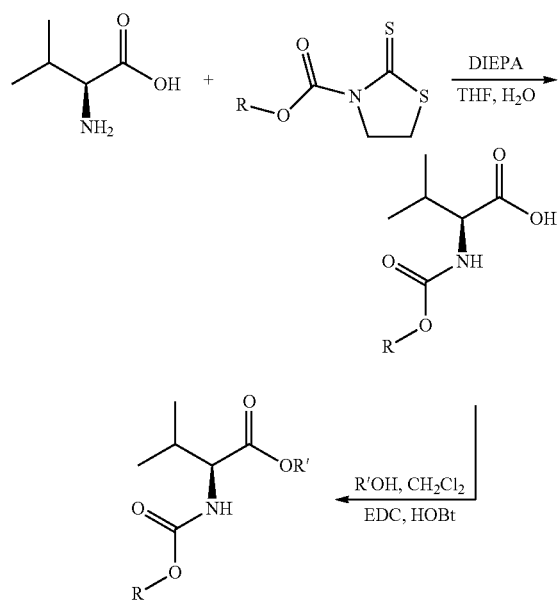
Scheme 4. Synthesis of amino acid conjugates: (R = terpene and/or vanilloid moiety)
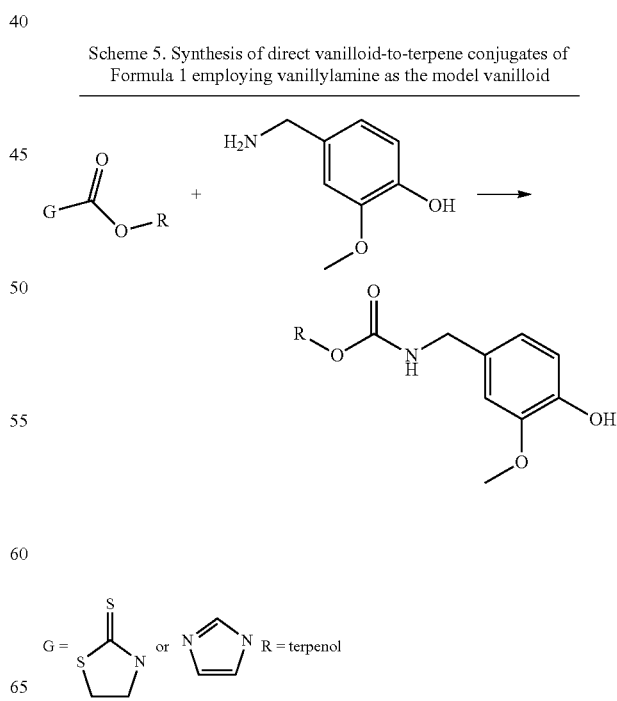
Scheme 5. Synthesis of direct vanilloid-to-terpene conjugates of Formula 1 employing vanillylamine as the model vanilloid

TABLE 1

Structural diversity consistent with the formulae of conjugates of the invention

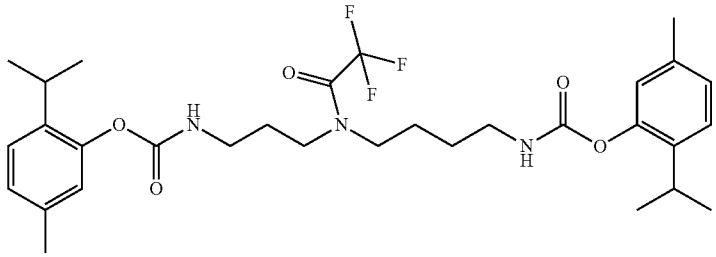 [SMILES: Cc1ccc(C(C)C)c(OC(=O)NCCCCN(CCCNC(=O)Oc2cc(C)ccc2C(C)C)C(=O)C(F)(F)F)c1]

NDH4616: 5-methyl-2-(propan-2-yl)phenyl [3-(trifluoroacetyl{4-[(5-methyl-2-(propan-2-yl)phenoxycarbonyl)amino]butyl}amino)propyl]carbamate

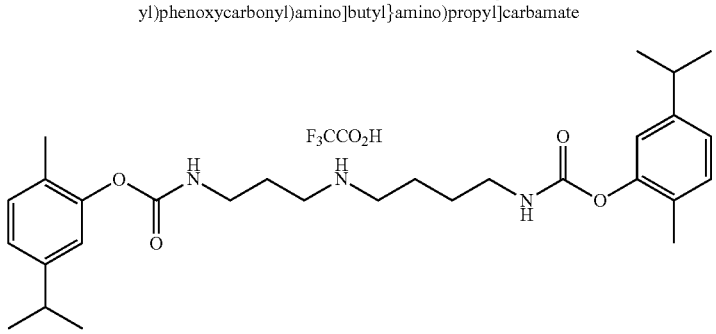

NDH4622: 2-methyl-5-(propan-2-yl)phenyl [3-({4-[(2-methyl-5-(propan-2-yl)phenoxycarbonyl)amino]butyl}amino)propyl]carbamate trifluoroacetic acid salt

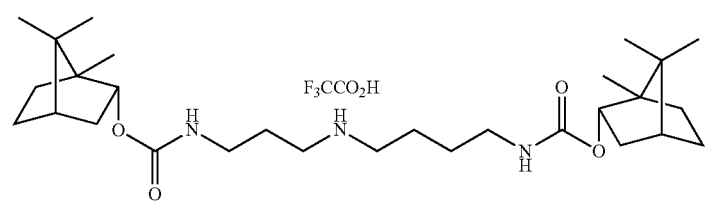 [SMILES: CC1(C)C2CCC1(C)C(OC(=O)NCCCCNCCCNC(=O)OC1CC3CCC1(C)C3(C)C)C2 ; "F3CCO2H"]

NDH4630: 1,7,7-trimethylbicyclo[2.2.1]hept-2-yl [3-({4-[(1,7,7-trimethylbicyclo[2.2.1]hept-2-yl oxycarbonyl)amino]butyl}amino)propyl]carbamate trifluoroacetic acid salt

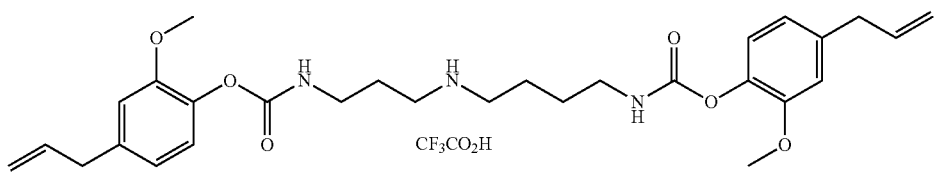 [SMILES: C=CCc1ccc(OC(=O)NCCCCNCCCNC(=O)Oc2ccc(CC=C)cc2OC)c(OC)c1 ; "CF3CO2H"]

NDH4635: 2-methoxy-4-(prop-2-en-1-yl)phenyl [3-({4-[(2-methoxy-4-(prop-2-en-1-yl)phenoxycarbonyl)amino]butyl}amino)propyl]carbamate trifluoroacetic acid salt

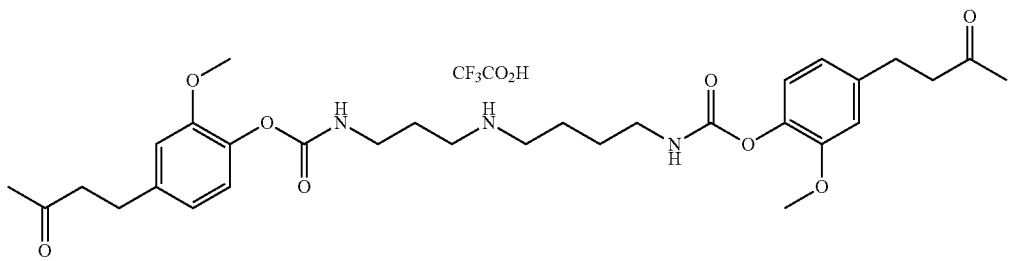 [SMILES: COc1cc(CCC(C)=O)ccc1OC(=O)NCCCCNCCCNC(=O)Oc1ccc(CCC(C)=O)cc1OC ; "CF3CO2H"]

NDH4637: 2-methoxy-4-(3-oxobutyl)phenyl [3-({4-[(2-methoxy-4-(3-oxobutyl)phenoxycarbonyl)amino]butyl}amino)propyl]carbamate trifluoroacetic acid salt TABLE 1-continued Structural diversity consistent with the formulae of conjugates of the invention

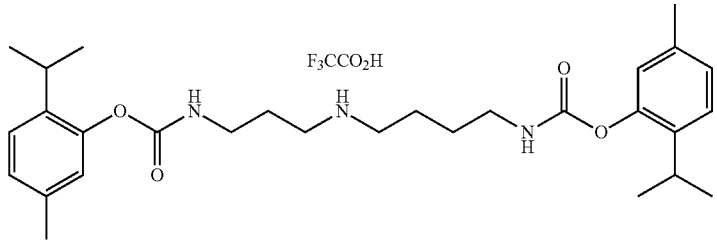 [SMILES: Cc1ccc(C(C)C)c(OC(=O)NCCCCNCCCNC(=O)Oc2cc(C)ccc2C(C)C)c1 ; "F3CCO2H"]

NDH4649: 5-methyl-2-(propan-2-yl)phenyl [3-({4-[(5-methyl-2-(propan-2-yl)phenoxycarbonyl)amino]butyl}amino)propyl]carbamate trifluoroacetic acid salt

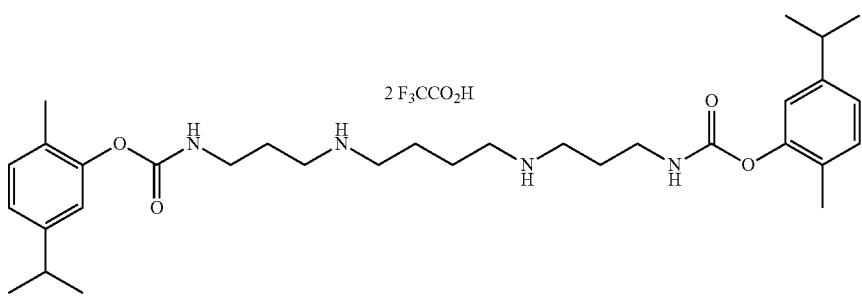

NDH4631: bis(5-isopropyl-2-methylphenyl)((butane-1,4-diylbis(azanediyl))bis(propane-3,1-diyl))dicarbamate

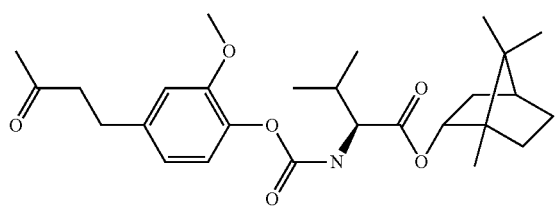 [SMILES: COc1cc(CCC(C)=O)ccc1OC(=O)N[C@H](C(=O)OC1CC2CCC1(C)C2(C)C)C(C)C]

NDH4638: (S)-(1R,2R,4S)-1,7,7-trimethylbicyclo[2.2.1]heptan-2-yl 2-(((2-methoxy-4-(3-oxobutyl)phenoxy)carbonyl)amino)-3-methylbutanoate

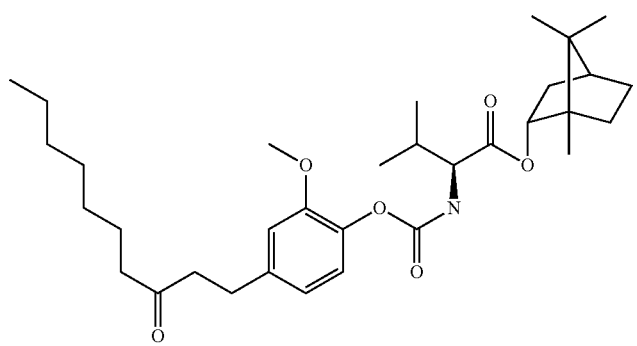 [SMILES: CCCCCCCC(=O)CCc1ccc(OC(=O)N[C@H](C(=O)OC2CC3CCC2(C)C3(C)C)C(C)C)c(OC)c1]

NDH4639: (S)-(1R,2R,4S)-1,7,7-trimethylbicyclo[2.2.1]heptan-2-yl 2-(((2-methoxy-4-(3-oxodecyl)phenoxy)carbonyl)amino)-3-methylbutanoate TABLE 1-continued Structural diversity consistent with the formulae of conjugates of the invention

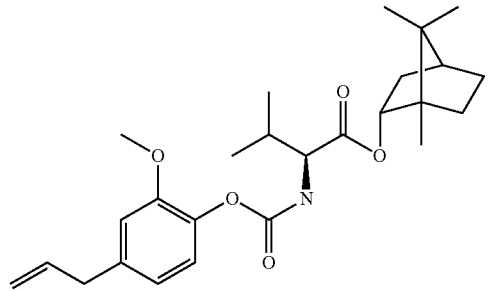 [SMILES: C=CCc1ccc(OC(=O)N[C@H](C(=O)OC2CC3CCC2(C)C3(C)C)C(C)C)c(OC)c1]

NDH4640: (S)-(1R,2R,4S)-1,7,7-trimethylbicyclo[2.2.1]heptan-2-yl 2-(((4-allyl-2-methoxyphenoxy)carbonyl)amino)-3-methylbutanoate

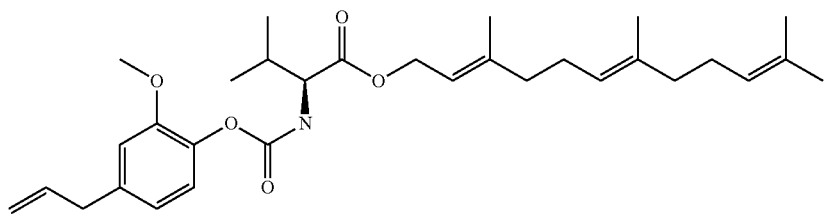 [SMILES: C=CCc1ccc(OC(=O)N[C@H](C(=O)OC/C=C(\C)CC/C=C(\C)CCC=C(C)C)C(C)C)c(OC)c1]

NDH4641: (S)-(2E,6E)-3,7,11-trimethyldodeca-2,6,10-trien-1-yl 2-(((4-allyl-2-methoxyphenoxy)carbonyl)amino)-3-methylbutanoate

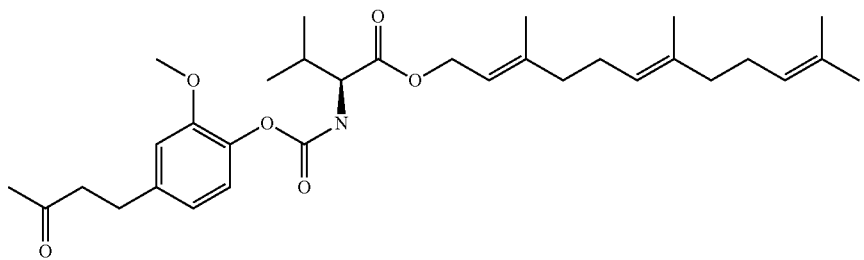 [SMILES: COc1cc(CCC(C)=O)ccc1OC(=O)N[C@H](C(=O)OC/C=C(\C)CC/C=C(\C)CCC=C(C)C)C(C)C]

NDH4642: (S)-(2E,6E)-3,7,11-trimethyldodeca-2,6,10-trien-1-yl 2-(((2-methoxy-4-(3-oxobutyl)phenoxy)carbonyl)amino)-3-methylbutanoate

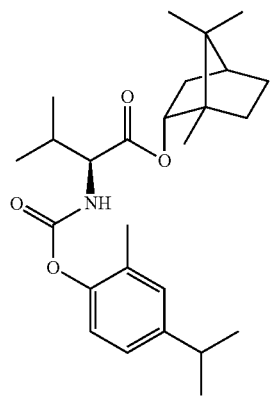 [SMILES: Cc1cc(C(C)C)ccc1OC(=O)N[C@H](C(=O)OC1CC2CCC1(C)C2(C)C)C(C)C]

NDH4647: (S)-(1R,2R,4S)-1,7,7-trimethylbicyclo[2.2.1]heptan-2-yl 2-(((4-isopropyl-2-methylphenoxy)carbonyl)amino)-3-methylbutanoate TABLE 1-continued Structural diversity consistent with the formulae of conjugates of the invention

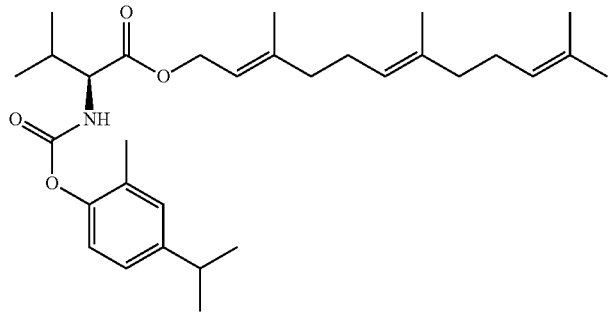 [SMILES: CC(C)=CCC/C(C)=C/CC/C(C)=C/COC(=O)[C@@H](NC(=O)Oc1ccc(C(C)C)cc1C)C(C)C]

NDH4648: (S)-(2E,6E)-3,7,11-trimethyldodeca-2,6,10-trien-1-yl 2-(((4-isopropyl-2-methylphenoxy)carbonyl)amino)-3-methylbutanoate

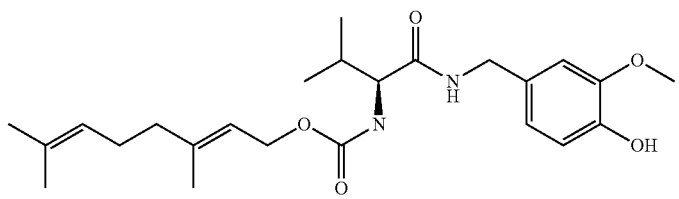 [SMILES: COc1cc(CNC(=O)[C@@H](NC(=O)OC/C=C(\C)CCC=C(C)C)C(C)C)ccc1O]

NDH4486: (S,E)-3,7-dimethylocta-2,6-dien-1-yl (1-((4-hydroxy-3-methoxybenzyl)amino)-3-methyl-1-oxobutan-2-yl)carbamate Preparation of Trifluoroacetic Acid Salts of Polyamines A) Formation of Protected Carbamates

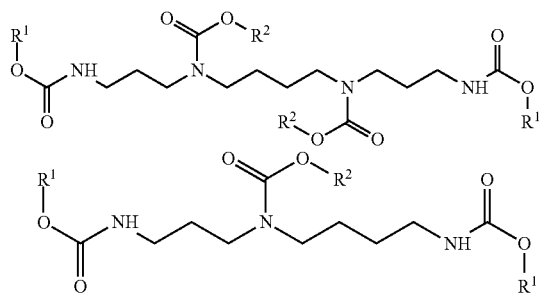

General Procedure (NDH4616, 4622, 4630, 4631, 4635, 4637 and 4649)

The polyamine (spermidine or spermine) was weighed into a round bottom flask containing a stirring bar. The amine was dissolved in dry dichloromethane (CH2Cl2) (10 mL/mmol). To the stirred solution at room temperature were added two equivalents of an alkyl or aryl 2-thioxo-1,3-thiazolidine-3-carboxylate (hereafter referred to as a thiazolidine carbamate) which rendered a yellow solution. The progress of the reaction was monitored by the loss of the yellow color as well as by TLC which revealed the release of 2-mercaptothiazoline (MTA) and the disappearance of the thiazolidine carbamate. After the first step was complete triethylamine (1 equivalent) was added to the reaction flask followed by the addition of Boc anhydride (Boc2) (1 equivalent). Once the second step was complete, as noted by TLC, the reaction solution was diluted with CH2Cl2, and the resulting solution was extracted with 1N HCl and then saturated NaCl. The organic layer was dried over MgSO4 (anhydrous), filtered, concentrated on the rotary evaporator and dried under vacuum. The crude material was covered with a solution of 7:3, hexanes/ethyl acetate (EtOAc) in order to crystallize out the released MTA. The supernatant was drawn off and concentrated. The product was purified by column chromatography on silica gel eluting with 7:3, hexanes/EtOAc.

1. NDH 4622: $R_f$=0.32 (7:3, hexanes/EtOAc); Yield=76%.
2. NDH 4630: $R_f$=0.39 (7:3, hexanes/EtOAc); Yield=57%.
3. NDH 4649: $R_f$=0.27 (7:3, hexanes/EtOAc); Yield=63%.
4. NDH 4631: Removal of MTA from the crude material was accomplished using 3:2, hexanes/EtOAc. Column purification was carried out using 96:4, $CH_2Cl_2$/acetone as eluant. $R_f$=0.25 (96:4, $CH_2Cl_2$/acetone); Yield=83%.
5. NDH 4635: The crude material was purified by column chromatography, without removing MTA, first using 98:2, $CH_2Cl_2$/MeOH and for the second column 96:4, $CH_2Cl_2$/acetone. $R_f$=0.21 (96:4, $CH_2Cl_2$/acetone): Yield=77%.
6. NDH 4637: The crude material was purified by column chromatography, without removing MTA, using a gradient of 94:6, $CH_2Cl_2$/acetone to 9:1, $CH_2Cl_2$/acetone and then 97:3, $CH_2Cl_2$/MeOH. $R_f$=0.06 (95:5, $CH_2Cl_2$/acetone); Yield=100%.
7. NDH 4616: Upon completion of the first step, 1.5 equivalents of ethyl trifluoroacetate were added in place of the $Boc_2$ and triethylamine, and the reaction mixture was stirred overnight. The product crystallized out of the reaction, and was collected by suction filtration and rinsed with $CH_2Cl_2$. Exact mass (ESI) calculated for $C_{29}H_{44}N_3O_4$ [M+H] 498.3326 found 498.3334. The exact mass represents the compound resulting from loss of the trifluoroacetyl group. $R_f$=0.70 (9:1, $CH_2Cl_2$/MeOH): mp=190-191° C.; Yield=51%.

B) Formation of Trifluoroacetic Acid (TFA) Salts

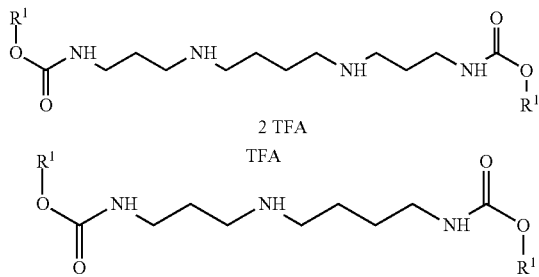

General procedure (NDH4616, 4622, 4630, 4631, 4635, 4637 and 4649)

The Boc-containing protected carbamate was dissolved in anhydrous CH2Cl2 (20 mL/mmol). Trifluoroacetic acid (4 mL/mmol) was added at room temperature. The reaction solution was stirred, and the progress of the reaction was monitored by TLC (7:3, hexanes/EtOAc). The deprotection was complete in 1-2 h. The volatiles were removed by distillation employing an aspirator vacuum. The residue was frozen on liquid N2 and dried under high vacuum. The dry product was covered with diisopropyl ether and the solid that separated was triturated and collected by suction filtration.

1. NDH 4622: Exact mass (ESI) calculated for $C_{29}H_{44}N_3O_4$ [M+H] 498.3326, found 498.3334. White powder; Yield=68%.
2. NDH 4631: Exact mass (ESI) calculated for $C_{32}H_{51}N_4O_4$ [M+H] 555.3905, found 555.3896. White solid; Yield=72%.
3. NDH 4649: Exact mass (ESI) calculated for $C_{29}H_{44}N_3O_4$ [M+H] 498.3326, found 498.3324. White solid; Yield=95%
4. NDH 4630: Exact mass (ESI) calculated for $C_{29}H_{52}N_3O_4$ [M+H] 506.3952, found 506.3973. Viscous oil; Yield=100%.
5. NDH 4635: The reaction was monitored by using 98:2, $CH_2Cl_2$/MeOH as the TLC solvent. The crude residue was covered with diethyl ether and triturated in order to isolate the pure product. Exact mass (ESI) calculated for $C_{29}H_4N_3O_6$ [M+H] 526.2912, found 526.2944. White powder; Yield=88%.
6. NDH 4637: The reaction was monitored using 96:4, $CH_2Cl_2$/acetone as the TLC solvent. The crude residue was covered with diethyl ether and triturated in order to isolate the pure product. Exact mass (ESI) calculated for $C_{31}H_{44}N_3O_8$ [M+H] 586.3123, found 586.3141. White solid; Yield=85%.

NMR Data

1) NDH 4622

$^1$HNMR (methanol-$d_4$) δ: 7.14-7.10 (m, 2H, 2xArH-3), 7.02-6.98 (m, 2H, 2xArH-4), 6.88-6.83 (m, 2H, 2xArH-6), 3.22 (bt, 2H, HNCH2CH2CH2N), 3.11-3.02 (m, 4H, CH2NHCH2), 2.89-2.81 (m, 2H, 2xHC(CH3)2), 2.15-2.11 (overlapping singlets, 6H, 2xAr-CH3), 1.97-1.89 (m, 2H, NHCH2CH2CH2NH), 1.79-1.69 (m, 2H, NHCH2CH2CH2-CH2NHCO), 1.69-1.60 (m, 2H, NHCH2CH2CH2CH2NHCO), and 1.22-1.18 (overlapping doublets, 12H, $^3$J=6.9 Hz, 2xArCH(CH3)2). Note: The protons OCHNCH2CH2CH2NH are masked beneath the methanol-d4 CH3 peak centered at δ3.30.

2) NDH 4630

$^1$HNMR (CDCl3+D2O) δ: 3.31 (bt, 2H, OCHNCH2CH2CH2NH), 3.17 (t, 2H, $^3$J=6.70 Hz, NHCH2CH2CH2CH2NHCO), 3.05-2.92 (m, 4H, CH2NHCH2), 2.36-2.24 (m, 2x1H, 3-H exo), 1.98-1.90 (m, 2H, NHCH2CH2CH2NH), 1.90-1.55 (m, 10 H, NHCH2CH2CH2CH2NHCO, 2xbornyl H-4, 2xbornyl H-5 exo and 2xbornyl H-6 endo), 1.30-1.16 (m, 4H, 2xbornyl H-5 endo and 2xbornyl H-6 exo), 1.00-0.94 (m, 2H, 2xbornyl H-3 endo), 0.88-0.86 (bd, 6H, 2xbornyl C-7 CH3), 0.85-0.83 (bd, 6H, 2xbornyl C-7 CH3) and 0.81 (bs, 6H, 2xbornyl C-1 CH3). Note: The bornyl C-2 protons are masked beneath the D2O peak.

3) NDH 4631

$^1$HNMR (methanol-$d_4$) δ: 7.16-7.10 (bd, 2H, 2xArH-3), 7.04-6.98 (m, 2H, 2xArH-4), 6.89-6.84 (bd, 2H, 2xAr-6), 3.11-2.99, (m, 8H, CH2NCH2CH2CH2CH2NCH2), 2.90-2.81 (m, 2H, 2xCH(CH3)2), 2.14 (bs, 6H, 2xArCH3), 1.97-1.89 (m, 4H, 2xNCH2CH2CH2N), 1.80-1.72 (m, 4H, NCH2CH2CH2CH2N), and 1.21 (bd, 12H, $^3$J=6.95 Hz, 2xHC(CH3)2). Note: The protons 2xOCNHCH2 are masked beneath the methanol-d4 CH3 peak centered at δ3.30.

4) NDH 4635

$^1$HNMR (methanol-$d_4$) δ: 6.98-6.90 (2 sets of doublets, 2H, $^3$J=8.0 and 8.05 Hz, 2xArH-6), 6.90-6.84 (2 sets of doublets, 2H, $^4$J=1.65 Hz, 2xArH-3), 6.79-6.71 (m, 2H, 2xArH-5), 60.1-5.90 (m, 2H, 2xCH2=CH), 5.12-5.01 (m, 4H, 2xCH2=CH), 3.80 (s, 3H, Ar-OCH3), 3.78 (s, 3H, Ar-OCH3), 3.36 (overlapping doublets, 4H, $^3$J=6.65 Hz, 2xArCH2—CH=CH2), 3.22-3.16 (m, 2H, NHCH2CH2CH2CH2NHCO), 3.12-3.00 (m, 4H, CH2NHCH2), 1.97-1.87 (m, 2H, NCH2CH2CH2N), 1.80-1.68 (m, 2H, NHCH2CH2CH2CH2NHCO), and 1.67-1.57 (m, 2H, NHCH2CH2CH2CH2NHCO). Note: The protons OCHNCH2CH2CH2NH are masked beneath the methanol-d4 CH3 peak centered at δ3.30.

5) NDH 4637

$^1$HNMR (methanol-$d_4$) δ: 6.96-6.87 (m, 4H, 2xArH-3 and 2xArH-6), 6.80-6.73 (m, 2H, 2xArH-5), 3.84-3.74 (m, 6H, 2xAr-OCH3), 3.21-3.14 (m, 2H, OCHNCH2CH2CH2NH), 3.12-3.00 (m, 4H, CH2NHCH2), 2.88-2.76 (m, 8H, 2xArCH2CH2CO), 2.12-2.11 (overlapping singlets, 6H, 2xCOCH3), 1.96-1.85 (m, 2H, NCH2CH2CH2N), 1.79-1.68 (m, 2H, NHCH2CH2CH2CH2NHCO) and 1.67-1.58 (m, 2H, NHCH2CH2CH2CH2NHCO). Note: The protons OCHNCH2CH2CH2NH are masked beneath the methanol-d4 CH3 peak centered at δ3.30.

6) NDH 4649

$^1$HNMR (methanol-$d_4$) δ: 7.24-7.13 (m, 2H, ArH-3), 7.06-6.95 (m, 2H, ArH-4), 6.86-6.75 (m, 2H, ArH-6), 3.25-3.21 (m, 2H, NHCH2CH2CH2CH2NHCO), 3.13-2.98 (m, 6H, 2xCH(CH3)2 and CH2NHCH2), 2.30 (bs, 6H, 2xArCH3), 1.99-1.88 (m, 2H, NCH2CH2CH2N), 1.82-1.70 (m, 2H, NHCH2CH2CH2CH2NCO) and 1.70-1.60 (m, 2H, NHCH2CH2CH2CH2NCO). Note: The protons OCNCH2CH2CH2NH are masked beneath the methanol-d4 CH3 peak centered at δ3.30.

7) NDH 4616

$^1$ HNMR (acetone-$d_6$) δ: 7.22 (bs, 2H (partially exchanged), 2xNH), 7.17 (apparent triplet, 2H, $^3$J=7.4 Hz, 2xArH-3), 6.98 (apparent triplet, 2H, $^3$J=7.8 Hz, 2xArH-4), 6.87 (s, 1H, ArH-6), 6.84 (s, 1H, ArH-6), 3.41-3.35 (m, 2H, HNCH2CH2CH2N), 3.28-3.16 (m, 6H, NHCH2CH2CH2NCH2CH2CH2CH2NH), 3.10-3.04 (m, 2H, Ar-CH(CH3)2),2.08 (m, 2H, HNCH2CH2CH2N), 1.93-1.84 (m, 2H,—NCH2CH2CH2CH2NH-), 1.72-1.65 (m, 2H, —NCH2CH2CH2CH2NH-) and 1.20-1.12 (overlapping doublets, 12H, $^3$J=6.85 Hz, 2xArCH(CH3)2).

Preparation of Valine-based Compounds
A) Carbamate Formation

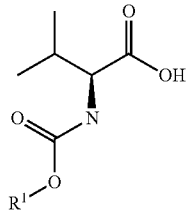

A flask containing a stirring bar was charged with the N-acyl thiazolidine-2-thione (1 eq) and L-valine (1.05 eq). To the flask was added THF (5 mL/mmol of the N-acyl thiazol-idine-2-thione), and the mixture was stirred until all the N-acyl thiazolidine-2-thione dissolved. Water (5 mL/mmol) was then added followed by N,N-diisopropyl-ethylamine (2 eq), and the resulting two-phase system was stirred vigorously at room temperature. The progress of the reaction was monitored by TLC (9:1, CH2Cl2/MeOH, v/v) and by the disappearance of the yellow color originating from the N-acyl thiazolidine-2-thione. When the reaction was complete, the solution was diluted with CH2Cl2 and extracted with 1N HCl. The organic layer was concentrated on the rotary evaporator, the residue taken up in Et2O, and the resulting ether layer was extracted with saturated NaHCO3. The aqueous layer was then washed with Et2O. The aqueous phase was acidified to pH=2-3 with 4N HCl. The resulting mixture was extracted with CH2Cl2. The organic layer was dried over MgSO4 (anhydrous), filtered, concentrated on the rotary evaporator and dried under high vacuum. The product was used in the next step without further purification.

B) Condensation Reactions
1. Amide Formation

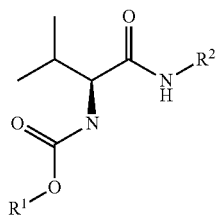

The N-acylated amino acid (1 eq), 1-Hydroxybenzotriazole (HOBt) (1.05 eq) and HMBA hydrochloride (1.05 eq) were placed in a round bottom flask equipped with a stirring bar and fitted with a rubber septum. Dry CH2Cl2 (4 mL/mmol) and NEt3 (1.05 eq) were added under positive N2 pressure via a syringe through the rubber septum. The flask was immersed in an ice bath, and the reaction mixture was stirred. After sufficient chilling, 1-Ethyl-3-(3-dimethyl-aminopropyl)carbodiimide (EDC) (1.05 eq) was added in one portion, and the reaction mixture was allowed to stir to room temperature overnight. TLC (96:4, CH2Cl2/MeOH, v/v) revealed completion of reaction. The reaction mixture was diluted with CH2Cl2 and washed with 1N HCl, H2O and saturated NaCl. The organic phase was dried over MgSO4 (anhydrous), filtered and concentrated on the rotary evaporator. The residue was dried under high vacuum, and the crude product was purified by column chromatography on silica gel eluting with 9:1, CH2Cl2/acetone, v/v.

NDH 4486: Mp=135-136° C.; $R_f$=0.54 (9:1, CH$_2$Cl$_2$/acetone); Yield=68%. Exact mass (ESI) calculated for C$_{24}$H$_{37}$N$_2$O$_5$ [M+H] 433.2697, found 433.2676.

2. Ester Formation

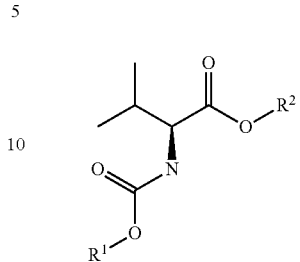

The preparation of esters was carried out as described for amides with the exception of replacing HOBt with 0.2 eq of DMAP. TLC analysis was performed using 7:3, hexanes/EtOAC, v/v while chromatographic purification was carried out using 8:2, hexanes/EtOAC, v/v.

1. NDH 4638: The crude material was purified by column chromatography eluting with 7:3, hexanes/EtOAc. $R_f$=0.27 (7:3, hexanes/EtOAc); Yield=47%. Exact mass (ESI) calculated for C$_{27}$H$_{40}$NO$_6$ [M+H] 474.2850, found 474.2878.

2. NDH 4642: The crude material was purified by column chromatography eluting with 7:3, hexanes/EtOAc. $R_f$=0.32 (7:3, hexanes/EtOAc); Yield=61%. Exact mass (ESI) calculated for C$_{32}$H$_{48}$NO$_6$ [M+H] 542.3476, found 542.3494.

3. NDH 4639: The reaction solution was concentrated, and the residue taken up in EtOAc. The organic layer was extracted with a small amount of water, saturated NaHCO$_3$, water, and finally saturated NaCl. The crude product was purified twice by column chromatography-first eluting with 8:2, hexanes/EtOAc and then 94:6, CH$_2$Cl$_2$/Et$_2$O. $R_f$=0.36 (8:2, hexanes/EtOAc); Yield=24%. Exact mass (ESI) calculated for C$_{33}$H$_{52}$NO$_6$ [M+H] 558.3789, found 558.3809.

4. NDH 4647: The reaction solution was concentrated, and the residue taken up in EtOAc. The organic layer was extracted with a small amount of water, saturated NaHCO$_3$, water, and finally saturated NaCl. The crude material was purified by column chromatography eluting with 8:2, hexanes/EtOAc. $R_f$=0.70 (8:2, hexanes/EtOAc); Yield=43%. Exact mass (ESI) calculated for C$_{26}$H$_{40}$NO$_4$ [M+H] 430.2952, found 430.2968.

5. NDH 4648: The reaction solution was concentrated, and the residue taken up in EtOAc. The organic layer was extracted with a small amount of water, saturated NaHCO$_3$, water, and finally saturated NaCl. The crude material was purified by column chromatography eluting with 8:2, hexanes/EtOAc. $R_f$=0.69 (8:2, hexanes/EtOAc); Yield=62%. Exact mass (ESI) calculated for C$_{31}$H$_{47}$NO$_4$Na [M+Na] 520.3397, found 520.3429.

6. NDH 4640: The reaction solution was concentrated, and the residue taken up in EtOAc. The organic layer was extracted with a small amount of water, saturated NaHCO$_3$, water, and finally saturated NaCl. The crude material was purified by column chromatography eluting with 8:1:1 (CH$_2$Cl$_2$/DIPE/hexanes). $R_f$=0.89 (8:1:1, CH$_2$Cl$_2$/DIPE/hexanes); Yield=57%. Exact mass (ESI) calculated for C$_{26}$H$_{38}$NO$_5$ [M+H] 444.2744, found 444.2750.

7. NDH 4641: The reaction solution was concentrated, and the residue taken up in EtOAc. The organic layer was extracted with a small amount of water, saturated NaHCO$_3$, water, and finally saturated NaCl. The crude material was purified by column chromatography eluting with 8:1:1 (CH$_2$Cl$_2$/DIPE/hexanes). $R_f$=0.92 (8:1:1, CH$_2$Cl$_2$/DIPE/ hexanes); Yield=64%. Exact mass (ESI) calculated for C$_{31}$H$_{46}$NO$_5$[M+H] 512.3370, found 512.3391.

NMR Data

1) NDH 4486
$^1$HNMR (CDCl$_3$) δ6.83 (d, 1H, $^3$J=8.0 Hz, ArH), 6.76 (d, 1H, $^4$J=1.85 Hz, ArH), 6.72 (dd, 1H, $^3$J=8.1 Hz, $^4$J=1.85 Hz, ArH), 6.12 (bs, 1H, amide NH), 5.57 (s, 1H, ArOH), 5.30 (bs, 1H, O—CH$_2$CH=), 5.16 (d,1H, $^3$J=7.4 Hz, carbamate NH), 5.06 (m, 1H, (CH$_3$)$_2$—C=CH—), 4.60-4.50 (m, 2H, C(O)O—CH$_2$-), 4.41-4.29 (2xdd, 2H, $^2$J=14.5 Hz, $^3$J=5.5 Hz, Ar-CH2-N), 3.93 (dd, 1H, $^3$J$_{NH}$=8.7 Hz, $^3$J$_{CH}$=6.1 Hz, CO—CH), 3.85 (s, 3H, Ar—O—CH$_3$), 2.22-2.10 (m, 1H, CH-(CH$_3$)$_2$), 2.10-2.08 (m,4H,=C—CH$_2$-CH$_2$-C=), 1.69-1.63 (m, 6H,=(CH$_3$)$_2$), 1.58 (s, 3H, CH$_3$-C=), 0.95 (d, 3H, $^3$J=6.8 Hz, CH(CH$_3$)-CH$_3$) and 0.90 (d, 3H, $^3$J=6.8 Hz, CH(CH$_3$)-CH$_3$). Exact mass (ESI) Calculated for C$_{24}$H$_{37}$N$_2$O$_5$ [M+1] 433.2697, found 433.2676.

2) NDH 4631
$^1$HNMR (methanol-d$_4$) δ7.16-7.10 (bd, 2H, 2xArH-3), 7.04-6.98 (m, 2H, 2xArH-4), 6.89-6.84 (bd, 2H, 2xAr-6), 3.11-2.99, (m, 8H, CH$_2$NCH$_2$CH$_2$CH$_2$CH$_2$NCH$_2$), 2.90-2.81 (m, 2H, 2xCH(CH$_3$)$_2$), 2.14 (bs, 6H, 2xArCH$_3$), 1.97-1.89 (m, 4H, 2xNCH$_2$CH$_2$CH$_2$N), 1.80-1.72 (m, 4H, NCH$_2$CH$_2$CH$_2$N), and 1.21 (bd, 12H, $^3$J=6.95 Hz, 2xHC(CH$_3$)$_2$). Note: The protons 2xOCNHCH2 are masked beneath the methanol-d$_4$ CH$_3$ peak centered at δ3.30.

3) NDH 4638
$^1$ HNMR (CDCl$_3$) δ6.97 (d, 1H, $^3$J=8.05 Hz, ArH-6), 6.75 (d, 1H, $^4$J=1.8 Hz, ArH-3), 6.71 (dd, 1H, $^3$J=8.05 Hz, $^4$J=1.8 Hz, ArH-5), 5.60 (d1H, $^3$J=9.05 Hz, NH), 4.90 (bd, 1H, $^3$J=9.55 Hz, bornyl H-2), 4.34 (dd, 1H, $^3$J=8.9 Hz, $^4$J=4.5 Hz, CO—CH), 3.77 (s, 3H, ArOCH$_3$), 2.85 (t, 2H, $^3$J=7.5 Hz, ArCH$_2$CH$_2$CO), 2.73 (t, 2H, $^3$J=7.45 Hz, ArCH$_2$CH$_2$CO), 2.41-2.36 (m, 1H, bornyl H-3exo), 2.27-2.20 (m, 1H, (CH$_3$)$_2$CH), 2.13 (s, 3H, COCH$_3$), 1.94-1.89 (m, 1H, bornyl H-6 endo), 1.78-1.72 (m, 1H, bornyl H-5 exo), 1.68 (t, 1H, J=4.40 Hz, bornyl H-4), 1.37-1.28 (m, 1H, bornyl H-6 exo), 1.25-1.16 (m, 1H, bornyl H-5 endo), 1.02 (d, 3H, $^3$J=6.85 Hz, CH$_3$(CH$_3$)CH-), 0.99-0.94 (m, 4H, bornyl H-3 endo and CH$_3$(CH$_3$)CH-), 0.89 (s, 3H, one bornyl C-7 CH$_3$), 0.87 (s, 3H, one bornyl C-7 CH$_3$) and 0.84 (s, 3H, bornyl C-1 CH$_3$).

4) NDH 4639
$^1$ HNMR (CDCl$_3$) δ6.97 (d, 1H, $^3$J=8.05 Hz, ArH-6), 6.75 (d, 1H, $^4$J=1.8 Hz, ArH-3), 6.71 (dd, 1H, $^3$J=8.10 Hz, $^4$J=1.8 Hz, ArH-5), 5.60 (d, 1H, $^3$J=8.95 Hz, NH), 4.91 (bd, 1H, $^3$J=9.60 Hz, bornyl H-2), 4.34 (dd, 1H, $^3$J=8.95 Hz, $^4$J=4.55 Hz, CHCO), 2.84 (t, 2H, $^3$J=7.58 Hz, ArCH2-), 2.69 (t, 2H, $^3$J=7.58 Hz, ArCH2CH$_2$CO-), 2.41-2.34 (m, 3H, bornyl H-3 exo and ArCH$_2$CH$_2$COCH$_2$-), 2.27-2.20 (m, 1H, (CH$_3$)$_2$CH-), 1.94-1.89 (m, 1H, bornyl H-6 endo), 1.78-1.72 (m, 1H, bornyl H-5 exo), 1.68 (t, 1H, $^3$J=4.42 Hz, bornyl H-4), 1.58-1.50 (m, —COCH$_2$CH$_2$(CH$_2$)$_4$CH$_3$ masked beneath D$_2$O peak), 1.36-1.17 (m, 10H, —COCH$_2$CH$_2$(CH$_2$)$_4$CH$_3$, bornyl H-5 endo and bornyl H-6 exo), 1.02 (d, 3H, $^3$J=6.85 Hz, CH$_3$(CH$_3$)CH-), 1.00-0.93 (m, 4H, CH$_3$(CH$_3$)CH- and bornyl H-3 endo) 0.89 (s, 3H, one bornyl C-7 CH3) and 0.86-0.83 (m, 9H, one bornyl C-7 CH$_3$, bornyl C-1 CH$_3$ and —CO(CH$_2$)$_6$CH$_3$).

5) NDH 4640
$^1$ HNMR (CDCl$_3$) δ7.01 (d, 1H, $^3$J=7.75 Hz, ArH-6), 6.75 (d, 1H, $^4$J=1.6 Hz, ArH-3), 6.73 (d, 1H, $^3$J=8.05 Hz, ArH-5), 5.97-5.89 (m, 1H, ArCH$_2$CH=CH2), 5.61 (d, 1H, $^3$J=8.95 Hz, NH), 5.10-5.04 (m, 2H, ArCH$_2$CH=CH$_2$), 4.92-4.89 (m, 1H, bornyl H-2), 4.35 (dd, 1H, J$_{NH}$=8.95 Hz, J$_{CH}$=4.55 Hz, —CH(NH)CO—), 3.80 (s, 3H, ArOCH$_3$), 3.34 (d, 2H, J=6.70 Hz, ArCH$_2$CH=CH$_2$), 2.42-2.34 (m, 1H, bornyl H-3 exo), 1.95-1.89 (m, 1H, bornyl H-6 endo), 1.78-1.71 (m, 1H, bornyl H-5 exo), 1.68 (t, 1H, J=4.45 Hz, bornyl H-4), 1.37-1.28 (m, 1H, bornyl H-6 exo), 1.25-1.16 (m, 1H, bornyl H-5 endo), 1.03 (d, 3H, $^3$J=6.90 Hz, CH$_3$(CH$_3$)CH—), 0.99-0.94 (m, 4H, bornyl H-3 endo and CH$_3$(CH$_3$)CH—), 0.89 (s 3H, one bornyl C-7 CH$_3$), 0.86 (s, 3H, one bornyl C-7 CH$_3$) and 0.84 (s, 3H, bornyl C-1 CH$_3$).

6) NDH 4641
$^1$ HNMR (CDCl$_3$) δ7.01 (d, 1H, $^3$J=8.0 Hz, ArH-6), 6.74 (d, 1H, $^4$J=1.65 Hz, ArH-3), 6.72 (dd, 1H, $^3$J=8.0 Hz, $^4$J=1.8 Hz, ArH-5), 5.96-5.88 (m, 1H, ArCH$_2$CH=CH$_2$), 5.60 (d, 1H, $^3$J=9.1 Hz, NH), 5.35 (bt, 1H, J=7.15 Hz, —OCH$_2$CH=C—), 5.13-5.03 (m, 4H, ArCH$_2$CH=CH$_2$ and 2 vinyl H of farnesyl chain), 4.72-4.61 (m, 2H, —OCH$_2$CH=C—), 4.33 (dd, 1H, J$_{NH}$=9.15 Hz, J$_{CH}$=4.6 Hz, (CH$_3$)$_2$CHCHCO), 2.25-2.17 (m, 1H, (CH$_3$)$_2$CH—), 2.13-1.93 (m, 8H, 4 allylic —CH$_2$- of farnesyl chain), 1.70 (s, 3H, —OCH$_2$C=C(CH$_3$)-), 1.66 (s, 3H, center CH$_3$ of farnesyl chain), 1.58 (s, 6H, —C=C(CH$_3$)$_2$), 0.996 (d, 3H, $^3$J=6.85 Hz, CH$_3$(CH$_3$) CH—) and 0.917 (d, 3H, $^3$J=6.90 Hz, CH$_3$(CH$_3$)CH—).

7) NDH 4642
$^1$ HNMR (CDCl$_3$) δ6.97 (d, 1H, $^3$J=8.0 Hz, ArH-6), 6.75 (d, 1H, $^4$J=1.85 Hz, ArH-3), 6.70 (dd, 1H, $^3$J=8.05 Hz, $^4$J=1.85 Hz, ArH-5), 5.60 (d, 1H, $^3$J=9.1 Hz, NH), 5.34 (m, 1H, —OCH$_2$CH=C—), 5.12-5.04 (m, 2H, 2 vinyl H of farnesyl chain), 4.72-4.60 (m, 2H, —OCH$_2$CH=C—), 4.33 (dd, 1H, J$_{NH}$=9.15 Hz, J$_{CH}$=4.6 Hz, (CH$_3$)$_2$CHCHCO), 3.79 (s, 3H, ArOCH$_3$), 2.84 (t, 2H, $^3$J=7.5 Hz, ArCH$_2$-), 2.73 (t, 2H, $^3$J=7.5 Hz, ArCH$_2$CH$_2$CO—), 2.26-2.17 (m, 1H, (CH$_3$)$_2$CH—), 2.12 (s, 3H, —COCH$_3$), 2.11-1.93 (m, 8H, 4 allylic —CH$_2$- of farnesyl chain), 1.70 (2, 3H, —OCH$_2$CH=C(CH$_3$)-), 1.66 (s, 3H, center CH$_3$ of farnesyl chain), 1.58 (s, 6H, —C=C(CH$_3$)$_2$), 0.99 (d, 3H, $^3$J=6.8 Hz, CH$_3$(CH$_3$)CH—) and 0.91 (d, 3H, $^3$J=6.90 Hz, CH$_3$(CH$_3$) CH—).

8) NDH 4647
$^1$ HNMR (CDCl$_3$) δ7.10 (d, 1H, $^3$J=7.75 Hz, ArH-6), 6.97 (dd, 1H, $^3$J=7.70 Hz, $^4$J=1.55 Hz, ArH-5), 6.91 (s, 1H, ArH-3), 5.54 (d, 1H, $^3$J=8.95 Hz, NH), 4.97-4.87 (m, 1H, bornyl H-2), 4.37 (dd, 1H, $^3$J=9.05 Hz and 4.45 Hz, COCH), 2.84 (septet, 1H, $^3$J=6.96 Hz, CH(CH$_3$)$_2$), 2.44-2.35 (m, 1H, bornyl H-3 exo), 2.30-2.21 (m, 1H, (CH$_3$)$_2$CHCH(NH)CO), 2.16 (s, 3H, ArCH$_3$), 1.96-1.88 (m, 1H, bornyl H-6 endo), 1.80-1.72 (m, 1H, bornyl H-5 exo), 1.71-1.67 ((bt, 1H, $^3$J=4.40 Hz, bornyl H-4), 1.37-1.29 (m, 1H, bornyl H-6 exo), 1.22-1.18 (m, 7H, bornyl H-5endo and ArCH(CH$_3$)$_2$), 1.03 (d, 3H, $^3$J=6.85 Hz, CH$_3$(CH$_3$)CHCH(NH)CO), 1.01-0.93 (m, 1H, bornyl H-3 endo), 0.95 (d, 3H, $^3$J=6.95 Hz, CH$_3$(CH$_3$)CHCH(NH)CO), 0.89 (s, 3H, bornyl C-7 CH$_3$), 0.87 (s, 3H, bornyl C-7 CH$_3$) and 0.84 (s, 3H, bornyl C-1 CH$_3$).

9) NDH 4648
$^1$ HNMR (CDCl$_3$) δ7.09 (d, 1H, $^3$J=7.75 Hz, ArH-2), 6.97 (dd, 1H, $^3$J=7.75 Hz, $^4$J=1.45 Hz, ArH-3), 6.90 (s, 1H, ArH-5), 5.54 (d, 1H, $^3$J=9.15 Hz, NH), 5.35 (bt, 1H, OCH$_2$—CH=), 5.12-5.04 (m, 2H, 2 vinyl protons), 4.75-4.61 (m, 2H, OCH$_2$—CH=), 4.38-4.32 (dd, 1H, $^3$J=9.18 Hz and $^3$J=4.58 Hz, CH—CO), 2.89-2.86 (septet, 1H, $^3$J=6.86 Hz, ArCH(CH$_3$)$_2$), 2.28-2.18 (m, 1H, (CH$_3$)$_2$CHCH(NH) CO), 2.15 (s, 3H, ArCH$_3$), 2.14-1.93 (m, 8H, 4 CH$_2$ units of farnesyl moiety), 1.71 (s, 3H, O—CH$_2$CH=C(CH$_3$)-), 1.66 (s, 3H, CH$_2$CH$_2$C=C(CH$_3$)CH$_2$-), 1.58 (s, 6H, C=C(CH$_3$)$_2$), 1.20 (d, 6H, $^3$J=6.95 Hz, ArCH(CH$_3$)$_2$), 1.00 (d, 3H, $^3$J=6.85 Hz, CH$_3$(CH$_3$)CHCH(NH)CO) and 0.92 (d, 3H, $^3$J=6.9 Hz, CH$_3$(CH$_3$)CHCH(NH)CO).

All references cited herein are incorporated herein by reference in their entireties.

What is claimed is:

1. An anti-inflammatory conjugate having the structure of:
   Formula 1A terpene-(carbamate)- vanilloid, or
   Formula 1B terpene-(carbamate)- terpene, or
   Formula 1C vanilloid-(carbamate)- vanilloid;
   wherein the terpenes of Formula D3 and the vanilloids of Formula IC are the same or different,
   wherein the terpene is selected from the group consisting of thymol, carvacrol, geraniol, nerol, farnesol, citronellol and linalool,
   wherein said vanilloid is independently selected from the group consisting of zingerone, eugenol, vanillyl alcohol, 3-methoxy-4-acetyloxybenzyl alcohol, paradol and vanillylamine.

2. The conjugate of claim 1, having the structure of Formula IA.

3. The conjugate of claim 1, having the structure of Formula IB.

4. The conjugate of claim 3, wherein said terpenes are the same.

5. The conjugate of claim 3, wherein said terpenes are different.

6. The conjugate of claim 1, having the structure of Formula IC.

7. The conjugate of claim 6, wherein said vanilloids are the same.

8. The conjugate of claim 6, wherein said vanilloids are different.

9. The conjugate of claim 1, wherein said terpenes are independently selected from the group consisting of geraniol, nerol, farnesol, citronellol, and linalool.

* * * * *